(12) United States Patent
Hsieh

(10) Patent No.: US 6,373,920 B1
(45) Date of Patent: Apr. 16, 2002

(54) METHOD AND APPARATUS FOR ACQUIRING CT PERFUSION IMAGES

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/681,312

(22) Filed: Mar. 16, 2001

(51) Int. Cl.⁷ .................................................. H05G 1/64
(52) U.S. Cl. ....................... 378/98.11; 378/8; 378/98.9; 382/131
(58) Field of Search ........................... 378/98.11, 98.12, 378/8, 98.9; 382/130, 131, 132; 250/363.01, 370.08, 370.03

(56) References Cited

U.S. PATENT DOCUMENTS

| | | | |
|---|---|---|---|
| 5,431,161 A | * 7/1995 | Ryals et al. ............... | 382/131 |
| 5,473,656 A | 12/1995 | Hsieh et al. | |
| 5,602,891 A | * 2/1997 | Pearlman ............... | 250/363.01 |
| 5,761,333 A | 6/1998 | Hsieh et al. | |
| 5,907,593 A | 5/1999 | Hsieh et al. | |
| 5,991,697 A | * 11/1999 | Nelson et al. ............ | 356/28.5 |
| 6,226,350 B1 | 5/2000 | Hsieh | |
| 6,210,333 B1 | * 4/2001 | Gardner et al. ............ | 600/450 |
| 6,215,841 B1 | 4/2001 | Hsieh | |
| 6,233,308 B1 | 5/2001 | Hsieh | |
| 6,236,706 B1 | 5/2001 | Hsieh | |

* cited by examiner

Primary Examiner—David P. Porta
(74) Attorney, Agent, or Firm—Carl B. Horton, Esq.; Armstrong Teasdale LLP

(57) ABSTRACT

Methods and apparatus for generating a difference image to determine perfusion parameters, such as mean transit time, cerebral blood flow, and cerebral blood volume utilizing a CT imaging system are described. To generate difference images, a difference projection data set including a first sub-set and a second sub-set of projection data is acquired. The first sub-set is obtained when no contrast medium is present in a patient or shortly after the contrast medium is injected into the patient. The second sub-set is obtained after the contrast medium is absorbed by the patient. The difference projection data is generated by subtracting the first sub-set from the second sub-set. The difference projection data then undergoes image reconstruction processing to generate the difference images. The difference images are then mapped to an image generated using the first sub-set, and perfusion parameters are determined utilizing the mapped difference image.

49 Claims, 2 Drawing Sheets

METHOD AND APPARATUS FOR ACQUIRING CT PERFUSION IMAGES

BACKGROUND OF THE INVENTION

This invention relates generally to methods and apparatus for CT imaging and other radiation imaging systems, and more particularly to utilizing CT images to determine perfusion parameters.

In at least some computed tomography (CT) imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at a detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged, so the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent to the scintillator. A group of x-ray attenuation measurements, i.e., projection data, from the detector array at one gantry angle is referred to as a view. A scan of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called CT numbers or Hounsfield units, which are used to control the brightness of a corresponding pixel on a cathode ray tube display.

To reduce the total scan time, a helical scan may be performed. To perform a helical scan, the patient is moved while the data for the prescribed number of slices is acquired. Such a system generates a single helix from a fan beam helical scan. The helix mapped out by a fan beam yields projection data from which images in each prescribed slice may be reconstructed.

At least one known CT imaging system utilizes a detector array and a data acquisition system (DAS) for collecting image data. The detector array includes detector cells or channels that each produce an analog intensity signal which is representative of the x-ray energy impinged upon the cell. The analog signals are then supplied to the DAS for conversion to digital signals. The digital signals are then used to produce image data. Detector cell degradation as measured by gain non-linearity typically produces ring or band annoyance artifacts.

CT perfusion methods are utilized to assess the viability of tissue of an organ-of-interest by determining perfusion parameters such as a mean transit time (MTT), a cerebral blood flow (CBF), and a cerebral blood volume (CBV). To determine perfusion parameters, the patient is continuously scanned at the same physical location, i.e., the patient table is stationary, and variations in the reconstructed CT images are measured. The image variations are then utilized to determine the perfusion parameters. Because the patient table is stationary, only a very limited volume of tissue can be examined by the CT scanner. For example, using a single slice CT scanner, sampling at 1000 views/second, the maximum volume that can be examined with a stationary patient table is approximately 10 mm. With a multi-slice CT scanner, the coverage is approximately 20 mm or 32 mm. Typically, a coverage range of 80–100 mm of anatomy is required to determine perfusion parameters.

Flat-panel based volumetric CT (VCT), on the other hand, is capable of covering a larger volume than a multi-slice CT scanner covering approximately 20 cm. A 40 cm by 40 cm flat-panel is capable of examining approximately a 20 cm volume, which is sufficient for a CT perfusion study of a human brain and a heart. A typical readout speed of a panel, however, is 30 views/second. Approximately one-thousand views are needed to ensure artifact-free image reconstruction. The time period to acquire one complete projection set is approximately 33 seconds, which is a protracted length of time compared to MTT and CBF. Even when detector channels in z-direction are ganged together across multiple slices, the acquisition time of a flat-panel based VCT is greater than a typical CT scanner acquisition time of 0.5–1.0 seconds.

SUMMARY OF INVENTION

Methods and apparatus for generating a difference image to determine perfusion parameters such as a mean transit time, a cerebral blood flow, and a cerebral blood volume utilizing a CT imaging system are described. To generate difference images, a difference projection data set is generated. A first sub-set of the projection data set is obtained when no contrast medium is present in a patient or shortly after the contrast medium is injected into the patient, i.e., before the contrast medium is sufficiently absorbed by the patient to impact collected data. A second sub-set of the projection data set is obtained after the contrast medium is absorbed by the patient, i.e., after up-take of the contrast medium. The difference projection data is generated by subtracting, for each view, the first sub-set of projection data from the second sub-set of projection data. The difference projection data then undergoes image reconstruction processing to generate the difference images. The difference images are then mapped to an image generated using the first sub-set of projection data, and perfusion parameters are determined utilizing the mapped difference image.

In another aspect, a processor in the imaging system is programmed to generate difference images and determine perfusion parameters using the difference images. To generate difference images, a difference projection data set is generated. The processor is configured to obtain a first sub-set of the projection data when no contrast medium is present in a patient or shortly after the contrast medium is injected into the patient, i.e., before the contrast medium is sufficiently absorbed by the patient to impact collected data. A second sub-set of projection data is obtained after the contrast medium is absorbed by the patient, i.e., after up-take of the contrast medium. The difference projection data is generated by subtracting, for each view, the first sub-set of projection data from the second sub-set of projection data. The difference projection data then undergoes image reconstruction processing to generate the difference images. The difference images are then mapped to an image generated using the first sub-set of projection data, and perfusion parameters are determined utilizing the mapped difference image.

In yet another aspect, a computer-readable medium in the imaging system is provided which comprises a record of difference projections used to reconstruct a difference image. To generate difference images, a record of difference projection data set is generated. A record of a first sub-set of projection data is obtained when no contrast medium is present in a patient or shortly after the contrast medium is absorbed by the patient to impact collected data. A record of a second sub-set of projection data is obtained after the contrast medium is absorbed by the patient, i.e., after up-take of the contrast medium. The record of difference projection data is generated by subtracting, for each view, the record of the first sub-set of projection data from the record of the second sub-set of projection data. Difference images are then reconstructed utilizing the records of difference projection data. The difference images are then mapped to an image generated using the first sub-set of projection data, and the perfusion parameters are determined utilizing the mapped difference image.

DETAILED DESCRIPTION

Figure 1:
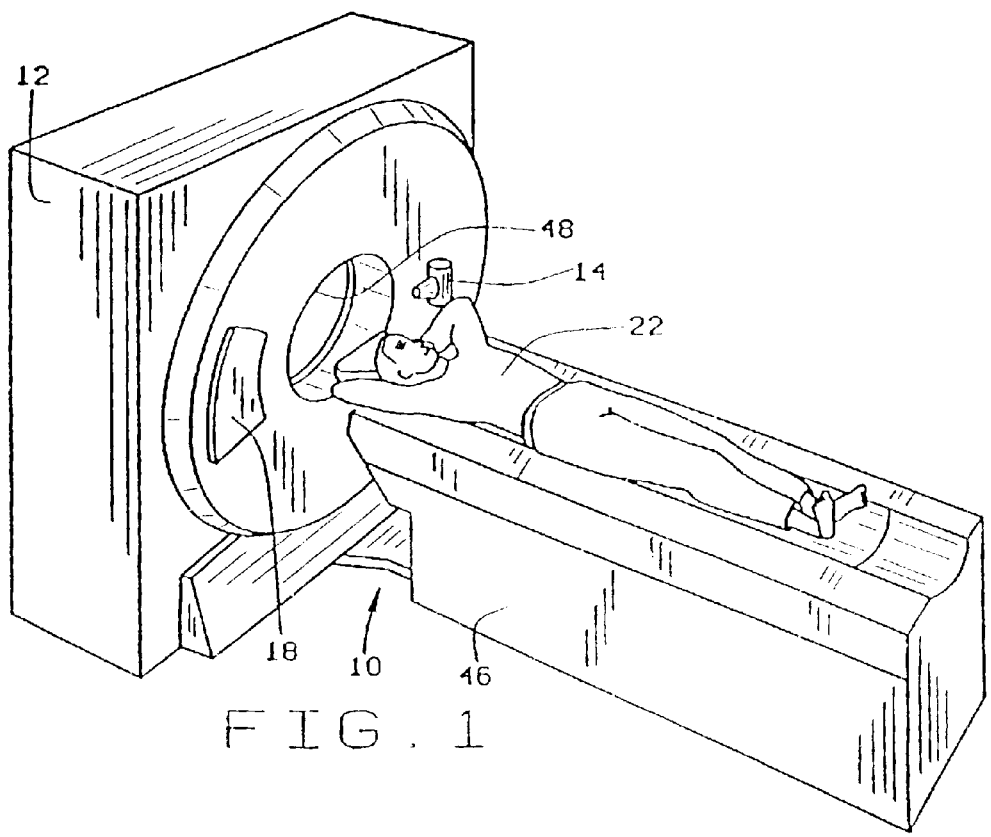
FIG. 1 is a pictorial view of a CT imaging system.
Figure 2:
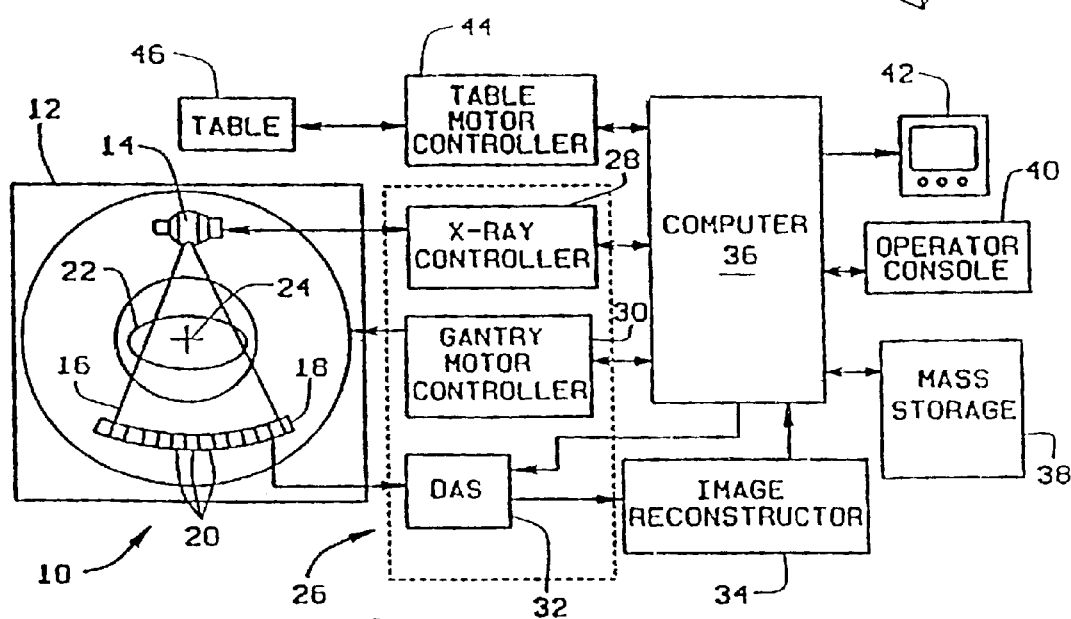
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In one embodiment, a third generation CT scanner with a digital flat panel read-out capable of imaging a 20 cm volume along a patient view axis is utilized.

Figure 3:
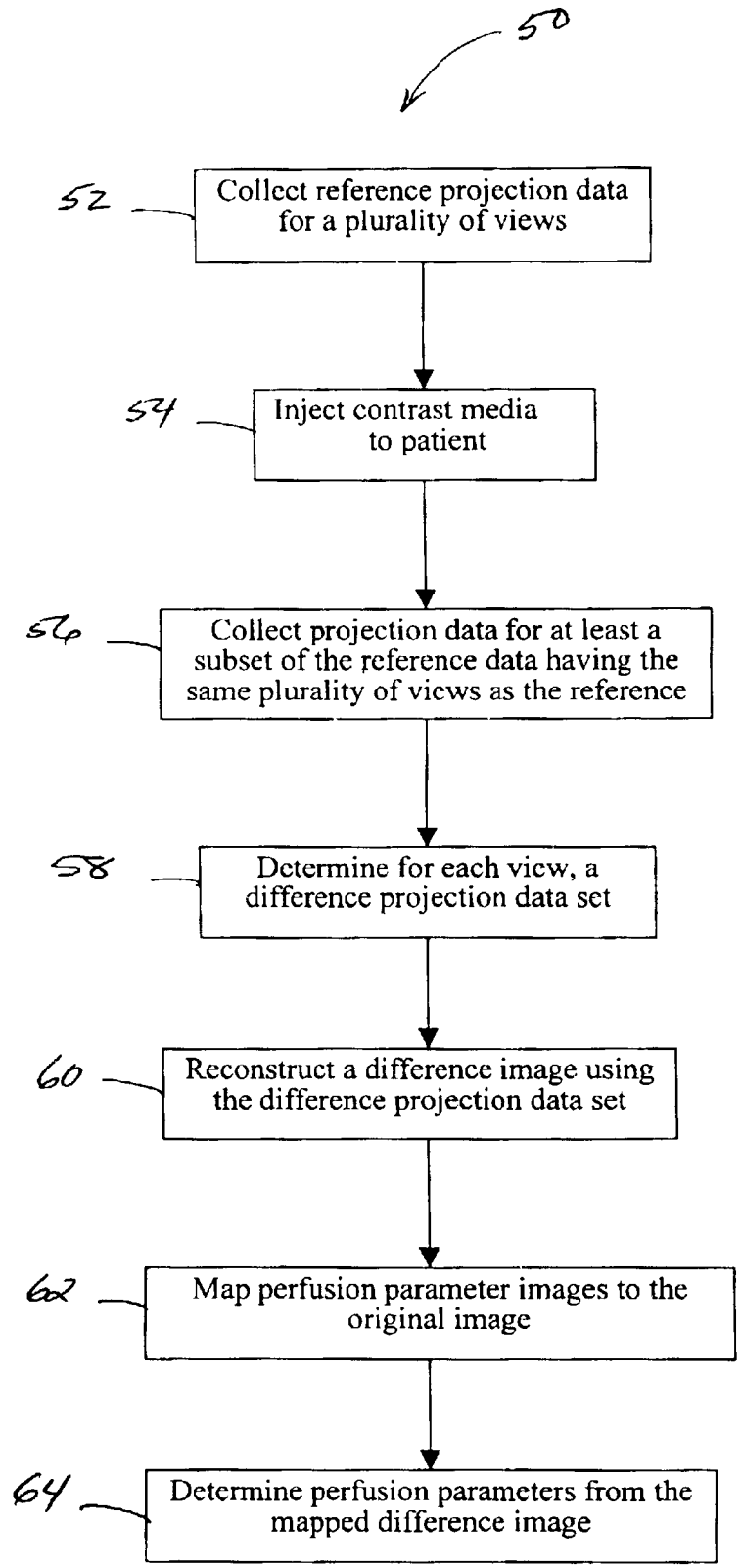
FIG. 3 is a flow chart illustrating the steps executed by the CT system to calculate perfusion parameters.

FIG. 3 is a flow chart 50 illustrating the steps executed to determine perfusion parameters. The method illustrated in FIG. 3 can be practiced by DAS 32 (shown in FIG. 2), image reconstructor 34 (shown in FIG. 2), or computer 36 (shown in FIG. 2). Generally, a processor in at least one of DAS 32, reconstructor 34, and computer 36 is programmed to execute the process steps described below. Of course, the method is not limited to practice in CT system 10 and can be utilized in connection with many other types and variations of imaging systems.

Referring specifically to FIG. 3, a set of scan data is acquired 52 with table 46 stationary. The scan data is pre-processed to generate a projection data. In one embodiment, a first sub-set of the projection data set is acquired prior to the injection 54 of contrast media to patient 22. In another embodiment, the first sub-set of projection data is acquired, or after, as the contrast media is injected into patient 22 but before the contrast medium is sufficiently absorbed by the patient to impact the collected data. The first sub-set of projection data is sometimes referred to herein as reference data. In one embodiment, the reference data set is acquired at a low speed, e.g. sixty projections per second, to enable an artifact free image reconstruction.

A second sub-set of projection data is acquired 56 after contrast media is absorbed by patient 22, i.e., after contrast media uptake. The second sub-set of projection data corresponds to the reference data set for each view. For example, in one embodiment, the reference data set is acquired during a single rotation of gantry 12 and a full-set of data is collected, e.g., approximately nine-hundred-and-eighty-four views are collected. The second sub-set of projection data is acquired faster than the reference data set. The second sub-set of projection data is acquired during a single rotation of gantry 12 and approximately sixty views are collected. In another embodiment, when the second sub-set of projection data is acquired, approximately thirty views are collected. The second sub-set of projection data is acquired before the contrast medium absorbed by the patient begins to dissipate from the tissues.

A difference projection data set is determined 58 by subtracting, for each view, the corresponding projection data in the reference data set from the second sub-set of projection data. In the difference projection data set, the human anatomy related structures are removed while data for vessels and tissues that have absorbed the contrast media remain. The projection data set is utilized to generate a difference image. Because projection data has to be acquired before the contrast medium dissipates from the tissues, e.g., the data must be collected quickly such that the amount of change between data sets is relatively small. There is not enough time to collect a complete set of views, e.g., approximately nine-hundred-eighty-four views. Therefore, approximately thirty to sixty views are collected for the second data set.

In one embodiment, an algebraic reconstruction technique is utilized to reconstruct 60 a set of difference images from the difference projection set. Of course, other image reconstruction techniques can be utilized. Once the difference image is generated, it is mapped 62, e.g., a one-to-one correspondence is performed, against an original image produced from the reference data set. The set of difference images is used to determine 64 perfusion parameters, e.g., MTT, CBF, and CBV, by comparing contrast uptake in the region of interest to contrast uptake in a main artery.

In one embodiment, a plurality of difference projections are determined and a difference image for each view is determined by subtracting the reference projection data from a particular projection acquisition. For example, the difference projection of the $1^{st}$ sub-set of projection data, e.g., reference projection data, and a $3^{rd}$ sub-set of projection data is used to determine the difference images at the time of the $3^{rd}$ projection acquisition. The difference image of the $3^{rd}$ projection acquisition is determined by subtracting the reference projection data from the $3^{rd}$ sub-set of projection data for the same view angles. Therefore, the difference image of an $n^{th}$ sub-set projection acquisition is determined by subtracting the reference projection data from the $n^{th}$ sub-set of projection data.

In an alternative embodiment, difference projections of adjacent projection sets are utilized to determine the difference image. For example, the difference projection of the $n^{th}$ sub-set of projection data and an $m^{th}$ sub-set of projection data is used to arrive at the difference image between the $n^{th}$ and the $m^{th}$ acquisition, where m>n. For instance, the difference projection of the $7^{th}$ projection acquisition is determined by subtracting the $6^{th}$ sub-set of projection data from the $7^{th}$ sub-set of projection data. In addition, the difference projection of the $8^{th}$ projection acquisition is determined by subtracting the $7^{th}$ sub-set of projection data from the $8^{th}$ sub-set of projection data. Of course, various incremental values can be utilized when determining a difference projection. For example, in one embodiment, an $8^{th}$ projection acquisition can be determined by subtracting the $6^{th}$ sub-set of projection data from the $8^{th}$ sub-set of projection data. Then the difference image is generated by accumulating the difference images of all prior acquisition pairs.

In yet another embodiment, CT system 10 includes a computer program residing on a computer-readable medium within mass storage 38 for reconstructing the difference image. The program includes a plurality of rules to reconstruct a difference image from a plurality of records of projection data stored on the computer-readable medium. The program utilizes a plurality of rules to determine perfusion parameters from the difference image.

For cardiac imaging, the heart is in continuous motion during the entire data acquisition period. Therefore, the difference image contains not only the difference due to the absorption of contrast media, but also the motion of the heart. As a result, the difference image contains higher frequency components, and an increased number of projection views are used in image reconstruction. Using an increased number of views results in prolonging the data acquisition which, in turn, is further influenced by heart motion.

To reduce the influence of the heart motion, in one embodiment, the data acquisition speed, e.g., gantry 12 rotation speed, is synchronized with the heart rate. The projections of the same angle will then correspond to the same phase of the heart motion. This same technique can be used to examine brain perfusion. Then, only a few projections, e.g., sixty projections, are used to accurately reconstruct the difference images due to contrast uptake.

In another embodiment, the difference images for a perfusion study are used to reduce cone-beam related artifacts. Specifically, the difference projections contain only low-contrast and low-frequency information. Therefore, cone beam related image artifact are suppressed by using cone beam reconstruction techniques, e.g., Feldkamp algorithm, to perform perfusion studies of relatively large cone angles.

While the invention has been described in terms of various specific embodiments, those skilled in the art will recognize that the invention can be practiced with modification within the spirit and scope of the claims.

What is claimed is:

1. A method to determine perfusion parameters, said method comprising the steps of:

acquiring a set of projection data including a first sub-set of projection data and a second sub-set of projection data;

generating a difference projection data set by subtracting the first sub-set of projection data from the second sub-set of projection data;

reconstructing a difference image from the difference projection data set; and determining perfusion parameters from the difference image.

2. A method in accordance with claim 1 wherein acquiring projection data further comprises the step of acquiring the first sub-set of projection data when no contrast media is injected into a patient.

3. A method in accordance with claim 1 wherein acquiring projection data further comprises the step of acquiring a first sub-set of projection data after contrast media is injected into a patient and before the contrast media is absorbed by the patient.

4. A method in accordance with claim 1 wherein acquiring projection data further comprises the step of acquiring a second sub-set of projection data after contrast media has been injected into a patient and absorbed by the patient.

5. A method in accordance with claim 1 wherein said step of acquiring a second sub-set of projection data further comprises the step of acquiring a second sub-set of projection data at the same projection angles as the first sub-set of projection data.

6. A method in accordance with claim 1 wherein determining a difference projection further comprises the step of subtracting an $n^{th}$ sub-set of projection data from the first sub-set of projection data.

7. A method in accordance with claim 1 wherein determining a difference projection further comprises the step of subtracting an $n^{th}$ sub-set of projection data from an $m^{th}$ sub-set of projection data, where m>n.

8. A method in accordance with claim 1 wherein reconstructing a difference image further comprises the step of executing a reconstruction algorithm.

9. A method in accordance with claim 1 wherein reconstructing a difference image comprises the step of executing a cone-beam reconstruction algorithm.

10. A method in accordance with claim 1 wherein determining perfusion parameters further comprises the step of mapping the difference image with an image generated from the first sub-set of projection data.

11. A method in accordance with claim 1 wherein determining perfusion parameters further comprises the step of determining at least one of a mean transit time, a cerebral blood flow, and a cerebral blood volume.

12. An imaging system comprising a computer, a gantry having a detector array, an x-ray source for radiating an x-ray beam along an imaging plane toward said detector array including a plurality of detector cells, said computer coupled to said x-ray source and said gantry, said imaging system configured to:

acquire a set of projection data comprising a first sub-set of projection data and a second sub-set of projection data;

generate a difference projection data set by subtracting said first sub-set of projection data from said second sub-set of projection data;

reconstruct a difference image from said difference projection data set; and determine perfusion parameters from said difference image.

13. An imaging system in accordance with claim 12 wherein said imaging system further comprises a patient table, said patient table configured to be stationary during acquisition of projection data.

14. An imaging system in accordance with claim 12 wherein said imaging system is configured to acquire said first sub-set of projection data when no contrast media is injected into a patient.

15. An imaging system in accordance with claim 12 wherein said imaging system is configured to acquire said first sub-set of projection data after contrast media is injected into a patient and before the contrast media is absorbed by the patient.

16. An imaging system in accordance with claim 12 wherein said imaging system is configured to acquire said second sub-set of projection data after contrast media has been injected into a patient and absorbed by the patient.

17. An imaging system in accordance with claim 12 wherein said imaging system is configured to acquire said second sub-set of projection data at the same projection angles as said first sub-set of projection data.

18. An imaging system in accordance with claim 12 wherein said imaging system is configured to determine said difference projection data set by subtracting said first sub-set of projection data from said $n^{th}$ sub-set of projection data.

19. An imaging system in accordance with claim 12 wherein said imaging system is configured to determine said difference projection data set by subtracting an $n^{th}$ sub-set of projection data from an $m^{th}$ sub-set of projection data, where m>n.

20. An imaging system in accordance with claim 12 wherein said difference image is configured to utilize a reconstruction algorithm.

21. An imaging system in accordance with claim 20 wherein said reconstruction algorithm comprises an algebraic reconstruction technique.

22. An imaging system in accordance with claim 12 wherein said imaging system is configured to map said difference image with an image generated from said first sub-set of projection data.

23. An imaging system in accordance with claim 12 wherein said perfusion parameters comprise at least one of a mean transit time, a cerebral blood flow, and a cerebral blood volume.

24. An imaging system in accordance with claim 11 wherein said imaging system is configured to reduce cone-beam artifact.

25. A processor programmed to reduce image artifact in a computed tomography imaging system, said processor configured to:

acquire a set of projection data comprising a first sub-set of projection data and a second sub-set of projection data;

generate a difference projection data set by subtracting said first sub-set of projection data from said second sub-set of projection data;

reconstruct a difference image from said difference projection data set; and determine perfusion parameters from said difference image.

26. A processor according to claim 25 wherein said processor is configured to acquire said first sub-set of projection data when no contrast media is injected into a patient.

27. A processor according to claim 25 wherein said processor is configured to acquire said first sub-set of projection data after contrast media is injected into a patient and before the contrast media is absorbed by the patient.

28. A processor according to claim 25 wherein said processor is configured to acquire said second sub-set of projection data after contrast media is injected into a patient and absorbed by the patient.

29. A processor according to claim 25 wherein said processor is configured to acquire said second sub-set of projection data at the same projection angles as said first sub-set of projection data.

30. A processor according to claim 25 wherein said processor is configured to subtract said first sub-set of projection data from an $n^{th}$ sub-set of projection data.

31. A processor according to claim 25 wherein said processor is configured to subtract an $m^{th}$ sub-set of projection data from an $n^{th}$ sub-set of projection data, where m>n.

32. A processor according to claim 25 wherein said processor is configured to utilize a reconstruction algorithm.

33. A processor according to claim 25 wherein said processor is configured to map said difference image with an image generated from said first sub-set of projection data.

34. A processor according to claim 25 wherein said processor is configured to reduce cone-beam image artifact.

35. A processor according to claim 25 wherein said processor is configured to determine at least one of a mean transit time, a cerebral blood flow, and a cerebral blood volume.

36. A computer-readable medium in an imaging system, said computer-readable medium comprising:

a record of a set of projection data comprising a record of a first sub-set of projection data and a record of a second sub-set of projection data;

a record of a difference projection generated by subtracting said record of said first sub-set of projection data from said record of said second sub-set of projection data;

a plurality of rules to reconstruct a difference image from said records of difference projections; and a function to determine perfusion parameters from said difference image.

37. A computer-readable medium according to claim 36 wherein said record of said first sub-set of projection data is generated when no contrast media is injected into a patient.

38. A computer-readable medium according to claim 36 wherein said record of said first sub-set of projection data is generated after contrast media is injected into a patient and before the contrast media is absorbed by the patient.

39. A computer-readable medium according to claim 36 wherein said record of said second sub-set of projection data is generated after contrast media is injected into a patient and absorbed by the patient.

40. A computer-readable medium according to claim 36 wherein said record of said difference projection comprises said record of said first sub-set of projection data subtracted from a record of an $n^{th}$ sub-set of projection data.

41. A computer-readable medium according to claim 36 wherein said record of said difference projection comprises a record of an $n^{th}$ sub-set of projection data subtracted from a record of an $m^{th}$ sub-set of projection data, where m>n.

42. A computer-readable medium according to claim 36 wherein said plurality of rules comprises a function to reconstruct said difference image from said difference projections.

43. A computer-readable medium according to 36 further comprising a function to map said difference image with an image generated from said first sub-set of projection data.

44. A computer-readable medium according to claim 36 wherein a plurality of rules comprise a function to reduce cone-beam image artifact.

45. A computer-readable medium according to claim 36 wherein said function to determine perfusion parameters comprises at least one of a mean transit time, a cerebral blood flow, and a cerebral blood volume.

46. A computer tomography imaging system comprising a computer, a patient table, a gantry having a detector array, an x-ray source for radiating an x-ray beam along an imaging plane toward said detector array including a plurality of detector cells, said computer coupled to said x-ray source and said gantry, and said patient table configured to be stationary during a scan, said computer tomography imaging system configured to:

acquire a set of projection data comprising a first sub-set of projection data and a second sub-set of projection data;

acquire said second sub-set of projection data at the same projection angles as said first sub-set of projection data;

generate a difference projection data by subtracting said first sub-set of projection data from said second sub-set of projection data;

reconstruct a difference image from said difference projection data utilizing an algebraic reconstruction technique to eliminate image-induced artifacts; map said difference image with an image generated from said first sub-set of projection data; and determine perfusion parameters from said difference image.

47. An imaging system in accordance to claim 46 wherein said difference projection data comprises said first sub-set of projection data subtracted from an $n^{th}$ sub-set of projection data.

48. An imaging system in accordance to claim 46 wherein said difference projection data comprises an $n^{th}$ sub-set of projection data subtracted from an $m^{th}$ sub-set of projection data, where m>n.

49. An imaging system in accordance with claim 46 wherein said perfusion parameters comprise at least one of a mean transit time, a cerebral blood flow, and a cerebral blood volume.

* * * * *

UNITED STATES PATENT AND TRADEMARK OFFICE
CERTIFICATE OF CORRECTION

PATENT NO.    : 6,373,920 B1
DATED         : April 16, 2002
INVENTOR(S)   : Jiang Hsieh It is certified that error appears in the above-identified patent and that said Letters Patent is hereby corrected as shown below:

Column 8,
Line 23, delete "$m^{th}$" and insert therefor -- $n^{th}$ --.
Line 24, delete "$n^{th}$" and insert therefor -- $m^{th}$ --.

Column 9,
Line 5, insert -- claim -- before "36".

Signed and Sealed this

Sixteenth Day of December, 2003

JAMES E. ROGAN
*Director of the United States Patent and Trademark Office*